US009056087B2

(12) United States Patent
Goldstein et al.

(10) Patent No.: US 9,056,087 B2
(45) Date of Patent: Jun. 16, 2015

(54) METHODS OF HEALING OR PREVENTING INFLAMMATION, DAMAGE AND OTHER CHANGES THAT OCCUR PRIOR TO, DURING OR IMMEDIATELY AFTER A MYOCARDIAL EVENT WITH THYMOSIN BETA 4, ANALOGUES, ISOFORMS AND OTHER DERIVATIVES

(75) Inventors: Allan L. Goldstein, Washington, DC (US); Jack Finkelstein, Jr., Chevy Chase, MD (US)

(73) Assignee: REGENERX BIOPHARMACEUTICALS, INC., Rockville, MD (US)

( * ) Notice: Subject to any disclaimer, the term of this patent is extended or adjusted under 35 U.S.C. 154(b) by 1046 days.

(21) Appl. No.: 10/488,084

(22) PCT Filed: Aug. 29, 2002

(86) PCT No.: PCT/US02/27520
§ 371 (c)(1),
(2), (4) Date: Aug. 6, 2004

(87) PCT Pub. No.: WO03/020215
PCT Pub. Date: Mar. 13, 2003

(65) Prior Publication Data
US 2004/0258680 A1    Dec. 23, 2004

Related U.S. Application Data

(60) Provisional application No. 60/315,347, filed on Aug. 29, 2001.

(51) Int. Cl.
*A61K 38/22* (2006.01)
*C07K 16/26* (2006.01)
*A61K 39/00* (2006.01)

(52) U.S. Cl.
CPC ....... *A61K 38/2292* (2013.01); *A61K 2039/505* (2013.01); *C07K 16/26* (2013.01)

(58) Field of Classification Search
USPC .......................................... 514/17
See application file for complete search history.

(56) References Cited

U.S. PATENT DOCUMENTS

| | | | | |
|---|---|---|---|---|
| 4,297,276 A | * | 10/1981 | Goldstein et al. | 530/324 |
| 4,543,340 A | | 9/1985 | Goldstein | |
| 5,578,570 A | | 11/1996 | Goldstein et al. | |
| 6,602,519 B1 | | 8/2003 | Stevenson et al. | |
| 7,268,118 B2 | | 9/2007 | Kleinman et al. | |
| 2002/0164794 A1 | * | 11/2002 | Wernet | 435/372 |
| 2007/0009469 A1 | | 1/2007 | Kleinman et al. | |
| 2007/0111931 A9 | * | 5/2007 | Kleinman et al. | 514/12 |

FOREIGN PATENT DOCUMENTS

| | | | |
|---|---|---|---|
| EP | 0 124 779 A2 | 11/1994 | |
| JP | 2-124815 A | 5/1990 | |
| JP | 3-178988 A | 8/1991 | |
| JP | 2000-103738 A | 4/2000 | |
| WO | WO 84/02274 A1 | 6/1984 | |
| WO | WO 94/11499 A1 | 5/1994 | |
| WO | WO 95/09646 A1 | 4/1995 | |
| WO | WO 96/11016 A1 | 4/1996 | |
| WO | WO 96/16983 A1 | 6/1996 | |
| WO | WO 97/48805 A1 | 12/1997 | |
| WO | WO 98/10071 A1 | 3/1998 | |
| WO | WO 99/49883 A2 | 10/1999 | |
| WO | WO 00/06190 | * 2/2000 | ............ A61K 38/22 |
| WO | WO 00/06190 A1 | 2/2000 | |

OTHER PUBLICATIONS

Grant et al ("Thymosin B4 Enhances Endothelial Cell Differentiation and Angiogenesis" J. Cell Sci. 108(1):3685-94, 1995; cited in the IDS of Apr. 2, 2009.*
Kovacic et al. Epithelial-to-mesenchymal and endothelial-to mesenchymal transition: From cardiovascular development to diseaseCirc. 2012; 125-1795-1808.*
Shin et al. Thymosin Beta4 Regulates Cardiac Valve Formation V/a Endothelial-Mesenchymal Transformation in Zebrafish Embryos. Mol. Cells 2014; 37(4): 330-336.*
Huff, T., et al., "B-Thymosins, small acidic peptides with multiple functions", *The International Journal of Biochem. & Cell Biology*, vol. 33 (2001), 205-220.
Huff, T., et al., "The dipyridyls paraquat and diquat attenuate the interaction of G-actin with thymosin B4", *FEBS Letters*, vol. 425 (1998), 495-498.
Malinda, K.M., et al., "Thymosin β4 stimulates directional migration of human umbilical vein endothelial cells", *The FASEB Journal*, 1997, vol. 11: 6, 474-481.
Sun, H-Q, et al., "β-Thymosins are not simple actin monomer buffering proteins", *The Journal of Biological Chemistry*, 1996, vol. 271, No. 16, 9223-9230.
Nimni, M.E., "Polypeptide growth factors: targeted delivery systems," *Biomaterials*, 1997, vol. 18, No. 18, 1201-1225.
Frank, S., et al., "Regulation of vascular endothelial growth factor expression in cultured keratinocytes," *Journal of Biological Chemistry*, 1995, vol. 270, No. 21, 12607-12613.
Sabolinski, M.L., et al., "Cultured skin as a 'smart material' for healing wounds: experience in venous ulcers," *Biomaterials*, 1996, vol. 17, No. 3, pp. 311-320.
Hannappel, E., et al. "Actin-sequestering ability of thymosin β4, thymosin β4 fragments, and thymosin β4-like peptides as assessed by the DNASE I inhibition assay," *Biol. Chem.*, 1993, vol. 374, 117-122.
Mihelic, M., et al., "Distribution and biological activity of B-thymosins," *Amino Acids*, 1994, vol. 6, No. 1, 1-13.
Bock-Marquette, I., et al. "Thymosin β4 activates integrin-linked kinase and promotes cardiac cell migration, survival and cardiac repair", *Nature*, 432, Nov. 25, 2004 , pp. 466-472.

(Continued)

*Primary Examiner* — Maury Audet
(74) *Attorney, Agent, or Firm* — Rothwell, Figg, Ernst & Manbeck, P.C.

(57) ABSTRACT

Inflammation or damage associated with myocardial events is treated or prevented by administration of an angiogenesis-inducing, anti-inflammatory peptide such as Thymosin β4, an isoform of Thymosin β4 or oxidized Thymosin β4.

9 Claims, No Drawings

(56) References Cited

OTHER PUBLICATIONS

Gomez-Marquez, et al. "High levels of mouse thymosin β4 mRNA in differentiating P19 embryonic cells and during development of cardiovascular issues", *Biochemica et Biophysica Acta*, 1306, 1996, pp. 187-193.
Runyan, R., et al. "Invasion of mesenchyme into three-dimensional collagen gels: a regional and temporal analysis of interaction in embryonic heart tissue", *Developmental Biology*, 95, 1983, pp. 108-114.
Smart, Nicola et al., "*Thymosin β4 Induces Adult Epicardial Progenitor Mobilization and Neovascularization*," Nature Publishing Group, vol. 445, pp. 177-182 (Jan. 11, 2007).
Supplementary Partial European Search Report, European Application No. EP 02 77 3255 dated Dec. 13, 2007.
Grant et al., "Thymosin β4 Enhances Endothelial Cell Differentiation and Angiogenesis" J. Cell Sci. 108(1):3685-94, 1995.
Tumbarello et al., Regulation of Paxillin Family Members During Epithelial-Mesenchymal Transformation: A Puptative Role for Paxillin 118:4849-4863, 2005.
Grant et al., "Thymosin β4 Enhances Endothelial Cell Differentiation and Angiogenesis" Angiogenesis 3(2):125-135, 1999.
Grant et al., "Matrigel Induces Thymosin β4 Gene in Differentiating Endothelial Cells" J. Cell Sci. 108(1):3685-3694, 1995.
Eadie et al., "C-Terminal Variations in Beta-Thymosin Family Members Specify Functional Differences in Actin-Binding Properties", J. Cell Biochem 77:277-287, 2000.
Hannappel, "Beta Thymosins" Ann. N.Y. Acad. Sci. 1112:21-37, 2007.
Herrmann et al., "Thypedin, the multi copy precursor for the hydra peptide pedin, is a Beta-thymosin repeat-like domain containing protein" Mechanisms of Development 122:1183-1193, 2005.
Hertzog et al., "The Beta-Thymosin/WH2 Domain: Structural Basis for the Switch from Inhibition to Promotion of Actin Assembly" Cell 117:611-623, 2004.
Huff et al., "Beta-Thymosins, small acidic peptides with multiple functions" Intl. J. Biochem. Cell. Biol. 33:205-220, 2001.
Irobi et al., "Structural basis of actin sequestration by thymosin-beta 4: implications for WH2 proteins" EMBO 23:3599-3608, 2004.
Malinda et al., "Thymosin Beta 4 Accelerates Wound Healing" The J. Inv. Derm. 11(3):364-368, 1999.
Paunola et al., "WH2 domain: a small, versatile adapter for actin monomers" FEBS Lett. 513:92-97, 2002.
Philp et al., "The actin binding site on thymosin beta 4 promotes angiogenesis" FASEB J. (online) 13 pages, 2003.
Rho et al., "The interaction between E-tropomodulin and thymosin beta-10 rescues tumor cells from thymosin beta-10 mediated apoptosis by restoring actin architecture" FEBS Lett. 557:57-63, 2004.
Vaduva et al., "Actin-binding Verprolin Is a Polarity Development Protein Required for the Morphogenesis and Function of the Yeast Actin Cytoskeleton" J. Cell Biol 139(7):1821-1833, 1997.
Vancompernolle et al., "The Interfaces of Actin and Acanthamoeba Actobindin" J. Biol. Chem. 266 (23):15427-15431, 1991.
Van Troys et al., "The actin binding site of thymosin beta 4 mapped by mutational analysis" EMBO J. 15(2): 201-210, 1996.
Vermeulen et al., "Solution structures of the C-terminal headpiece subdomains of human villin and advillin, evaluation of headpiece F-actin-binding requirements" Protein Sci. 13:1276-1287, 2004.
Wyczolkowska et al., "Thymosin Beta 4 and thymosin Beta 4-derived peptides induce mast cell exocytosis" Peptides, 28:752-759, 2007.
Bock-Marquette et al. "Thymosin β4 activates integrin-linked kinase and promotes cardiac cell migration, survival and cardiac repair" Nature 432:466-472, 2004.
Crockford "Development of Thymosin β4 for Treatment of Patients with Ischemic Heart Disease" Ann. N.Y. Acad. Sci. 1112:385-395, 2007.
Fibrex Medical Inc.: "Fibrex Medical Initiates Phase II Trial of Treatment for Reperfusion Injury in Myocardial Infarction," printed from http://www.fibrexmedical.com/news_1.html, 8 pages, 2007.

"FX06 Peptide for Myocardial Infarction Proves to be Safe, Fibrex Medical," printed from http://www.medicalnewstoday.com/printerfriendlynew.php?newsid=41250, 1 page, 2007.
Gnecchi et al. "Evidence supporting paracrine hypothesis for Akt-modified mesenchymal stem cell-mediated cardiac protection and functional improvement" FASEB J. 20:661-669, 2006.
Goldstein et al. "Acceleration of Lymphoid Tissue Regeneration in X-Irradiated CBA/W Mice by Injection of Thymosins" Rad. Res. 41:579-593, 1970.
Goldstein et al.: "Purification and Biological Activity of Thymosin, a Hormone of the Thymus Gland," Proceedings of the Natl. Acad. Sci., 69(7):1800-1803, 1972.
Gomez-Marquez et al. "High levels of mouse thymosin β4 mRNA in differentiating P19 embryonic cells and during development of cardiovascular tissues" Biochimica et Biophysica Acta 1306:187-193, 1996.
Gomez-Marquez "Function of Prothymosin α in Chromatin Decondensation and Expression of Thymosin β-4 Linked to Angiogenesis and Synaptic Plasticity" Ann. N.Y. Acad. Sci. 1112:201-209, 2007.
Grant et al. "Thymosin β4 enhances endothelial cell differentiation and angiogenesis" Angiogenesis 3:125-135, 1999.
Hahn "Thymuskin: Clinical Efficacy, Biological Effects, Modes of Action," 6 pages, 2006.
Hannappel et al. "Isolation Peptides from Calf Thymus," Biochem. and Biophys. Res. Comm. 104(1):266-271, 1982.
Hinkel et al. "Rapid eEPC-Mediated Cardioprotection after Ischemia/Reperfusion: Influence of Thymosin Beta 4 Expression" Abstracts of J. Vasc. Res. 43:534-535, 2006.
Hinkel et al. "Cardioprotective potential of Thymosin β4 after Ischemia/Reperfusion in a Preclinical Pig Model" Basic Science Abstract Suppl. II 116(16):II-130, 2007.
Li et al. "Thymosin beta 4 regulation, expression and function in aortic valve interstitial cells" J. Heart Valve Dis. 11:726-735, 2002.
Low et al. "Complete amino acid sequence of bovine thymosin $β_4$: A thymic hormone that induces terminal deoxynucleotidyl transferase activity in thymocyte populations," Proc. Natl. Acad. Sci. USA, 78(2):1162-1166, 1981.
"New Study Confirms TB4 Improves Cardiovascular Function after Heart Attack," 2 pages, 2006.
Peng et al. "Antifibrotic effects of N-acetyl-seryl-aspartyl-Lysyl-proline on the heart and kidney in aldosterone-salt hypertensive rats" Hypertension 37(2 Part 2):794-800, 2001.
Peng "Ac-SDKP Reverses Cardiac Fibrosis in Rats With Renovascular Hypertension", Hypertension 42:1164-1170, 2003.
Regenerx Corporate Presentation (retrieved from http://www.regenerx.com/pdf/NCInvestorPresentation_v38.ppt on Apr. 13, 2009, 34 pages).
Rhaleb et al. "Long-term effect of N-acetyl-seryl-aspartyl-lysyl-proline on left ventricular collagen deposition in rats with w-kidney, 1-clip hypertension" Circulation. 103(25):3136-41, 2001.
Rossdeutsch et al. "Thymosin β4 and Ac-SKDP: Tools to mend a broken heart" J. Mol. Med. DOI 10.1007/s00109-007-0243-9, 7 pages, 2007.
Runyan et al. "Invasion of Mesenchyme into Three-Dimensional Collagen Gels: A Regional and Temporal Analysis of Interaction in Embryonic Heart Tissue" Dev. Biol. 95:108-114, 1983.
Schneider "Prometheus unbound" Nature 432:451-453, 2004.
Simenel et al. "Structural requirements for thymosin β4 in its contact with actin" Eur. J. Biochem. 267:3530-3538, 2000.
Smart et al., "Thymosin β4 induces adult epicardial progenitor mobilization and neovascularization" Nature 445:177-182, 2007.
Srivastava et al., "Thymosin β4 is Cardioprotective after Myocardial Infarction" Ann. N.Y. Acad. Sci. 1112:161-170, 2007.
Vancompernolle et al. "The Interfaces of Actin and Acanthamoeba Actobindin" J. Bio. Chem. 266(23):15427-15431, 1991.
Vancompernolle et al. "G- to F-actin modulation by a single amino acid substitution in the actin binding site of actobindin and thymosin B4" EMBO J. 11(13):4739-46, 1992.
Yang, F., "Ac-SDKP Reverses Inflammation and Fibrosis in Rats With Heart Failure After Myocardial Infarction", Hypertension, 43:229-236, 2004.

(56) References Cited

OTHER PUBLICATIONS

R. Markwald et al.: "The next frontier in cardiovascular development biology—an integrated approach to adult disease?" Nature Clinical Practice Cardiovascular Medicine, vol. 4, No. 2, Feb. 2007, pp. 60-61.

I. Bock-Marquette et al.: "Thymosin β4 mediated PKC activation is essential to initiate the embryonic coronary developmental program and epicardial progenitor cell activation in adult mice in vivo," Journal of Molecular and Cellular Cardiology, vol. 46, 2009, pp. 728-738.

S. Shrivastava et al.: "Thymosin β4 and cardiac repair," Annals of the New York Academy of Sciences, vol. 1194, 2010, pp. 87-96.

N. Smart et al.: "Thymosin β4 induces adult epicardial progenitor mobilization and neovascularization," Nature, vol. 445, Jan. 11, 2007, pp. 177-182.

I. Bock-Marquette et al.: "Thymosin β4 activates integrin-linked kinase and promotes cardiac cell migration, survival and cardiac repair," Nature, vol. 432, Nov. 25, 2004, pp. 466-472.

N. Sopko et al.: "Significance of Thymosin β4 and Implication of PINCH-1-ILK-α-Parvin (PIP) Complex in Human Dilated Cardiomyopathy," PLoS One, vol. 6, iss. 5, May 2011, pp. 1-10.

S. Lv et al.: "Relationship between serum thymosin β4 levels and coronary collateral development," Coronary Artery Disease, 2011, pp. 1-4.

M. Lakkis et al.: "Neurofibromin modulation of ras activity is required for normal endocardial-mesenchymal transformation in the developing heart," Development, vol. 125, 1998, pp. 4359-4367.

M. Azhar et al.: "Ligand-Specific Function of Transforming Growth Factor Beta in Epithelial-Mesenchymal Transition in Heart Development," Developmental Dynamics, vol. 238, No. 2, Feb. 2009, pp. 431-442.

Japanese Office Action issued in JP Appln. No. 123032/2009, mailed Nov. 29, 2011, with English translation, 18 pages.

\* cited by examiner

METHODS OF HEALING OR PREVENTING INFLAMMATION, DAMAGE AND OTHER CHANGES THAT OCCUR PRIOR TO, DURING OR IMMEDIATELY AFTER A MYOCARDIAL EVENT WITH THYMOSIN BETA 4, ANALOGUES, ISOFORMS AND OTHER DERIVATIVES

CROSS-REFERENCE TO RELATED APPLICATION

The present application is a National Phase Application of International Application No. PCT/US02/27520, filed Aug. 29,2002, which claims the benefit of U.S. Provisional Application Ser. No. 60/315,347, filed Aug. 29, 2001.

BACKGROUND OF THE INVENTION

1. Field of the Invention

The present invention relates to the field of healing or preventing inflammation, damage and other changes that occur in the heart, heart valves and septa just prior to, during or immediately after a myocardial event (e.g., myocardial infarction).

2. Description of the Background Art

There are many causes of myocardial and coronary vessel and tissue injuries, including but not limited to myocardial ischemia, clotting, vessel occlusion, infection, developmental defects or abnormalities and other such myocardial events. Myocardial infarction results from blood vessel disease in the heart. It occurs when the blood supply to part of the heart is reduced or stopped (caused by blockage of a coronary artery). The reduced blood supply causes injuries to the heart muscle cells and may even kill heart muscle cells. The reduction in blood supply to the heart is often caused by narrowing of the epicardial blood vessels due to plaque. These plaques may rupture causing hemorrhage, thrombus formation, fibrin and platelet accumulation and constriction of the blood vessels.

There remains a need in the art for improved methods and compositions for healing or preventing inflammation, damage and other changes that occur prior to, during or immediately after a myocardial event.

SUMMARY OF THE INVENTION

In accordance with the present invention, a method of treatment for promoting healing or prevention of damage associated with myocardial events involves administration to a subject or patient in need of such treatment an effective amount of a composition comprising an angiogenesis-inducing and anti-inflammatory polypeptide comprising amino acid sequence LKKTET [SEQ ID NO: 1] or a conservative variant thereof having myocardial event-inhibiting activity.

DETAILED DESCRIPTION OF THE INVENTION

The present invention is based on a discovery that actin-sequestering peptides such as thymosin β4 (Tβ4)) and other actin-sequestering peptides or peptide fragments containing amino acid sequence LKKTET [SEQ ID NO: 1] or conservative variants thereof, promote healing or prevention of damage and other changes associated with myocardial events. Included are N- or C-terminal variants such as KLKKTET [SEQ ID NO: 2] and LKKTETQ [SEQ ID NO: 3]. Tβ4 has been suggested as being a factor in angiogenesis in rodent models. However, there heretofore has been no known indication that such properties may be useful in treating myocardial and coronary vessel events such as myocardial infarction, vessel occlusion or heart valve defects and damage. Without being bound to any particular theory, these peptides may have the capacity to promote repair, healing and prevention by having the ability to induce terminal deoxynucleotidyl transferase (a non-template directed DNA polymerase), to decrease and modulate the levels of one or more inflammatory cytokines or chemokines, and to act as a chemotactic and/or angiogenic factor for endothelial cells and thus heal and prevent degenerative changes in patients afflicted with myocardial events.

The present invention provides factors and compositions that can enhance or down regulate mesenchymal epithelial cell differentiation and restore the functionality of damaged myocardium tissue and vessels due to the effects of ischemia, infection, aging, and other insult or injury.

Thymosin β4 was initially identified as a protein that is up-regulated during endothelial cell migration and differentiation in vitro. Thymosin β4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration and vascularization.

In accordance with one embodiment, the invention is a method of treatment for promoting healing and prevention of damage and inflammation associated with myocardial events comprising administering to a subject in need of such treatment an effective amount of a composition comprising an angiogenesis-inducing, anti-inflammatory peptide comprising amino acid sequence LKKTET[SEQ ID NO:1], or a conservative variant thereof having angiogenesis-inducing, anti-inflammatory activity, preferably Thymosin β4, an isoform of Thymosin β4, oxidized Thymosin β4, Thymosin β4 sulfoxide, or an antagonist of Thymosin β4.

Compositions which may be used in accordance with the present invention include Thymosin β4 (Tβ4), Tβ4 isoforms, oxidized Tβ4, Thymosin β4 sulfoxide, polypeptides or any other actin sequestering or bundling proteins having actin binding domains, or peptide fragments comprising or consisting essentially of the amino acid sequence LKKTET [SEQ ID NO:1] or conservative variants thereof, having angiogenesis-inducing, anti-inflammatory activity. International Application Serial No. PCT/US99/17282, incorporated herein by reference, discloses isoforms of Tβ4 which may be useful in accordance with the present invention as well as amino acid sequence LKKTET [SEQ ID NO:1] and conservative variants thereof having angiogenesis-inducing, anti-inflammatory activity, which may be utilized with the present invention. International Application Serial No. PCT/GB99/00833 (WO 99/49883), incorporated herein by reference, discloses oxidized Thymosin β4 which may be utilized in accordance with the present invention. Although the present invention is described primarily hereinafter with respect to Tβ4 and Tβ4 isoforms, it is to be understood that the following description is intended to be equally applicable to amino acid sequence LKKTET [SEQ ID NO:1], LKKTETQ [SEQ ID NO:3], peptides and fragments comprising or consisting essentially of LKKTET [SEQ ID NO:1] or LKKTETQ [SEQ ID NO:3], conservative variants thereof having angiogenesis-inducing, anti-inflammatory activity, as well as oxidized Thymosin β4.

In one embodiment, the invention provides a method for healing and preventing inflammation and damage in a subject by contacting the damaged site with an effective amount of an angiogenesis-inducing, anti-inflammatory composition which contains Tβ4 or a Tβ4 isoform. The contacting may be direct or systemically. Examples of contacting the damaged site include contacting the site with a composition comprising Tβ4 alone, or in combo with at least one agent that enhances Tβ4 penetration, or delays or slows release of Tβ4 peptides into the area to be treated. Administration may include, for example, intravenous, intraperitoneal, intramuscular or subcutaneous injections, or inhalation, transdermal or oral administration of a composition containing Tβ4 or a Tβ4 isoform, etc. A subject may be a mammal, preferably human.

Tβ4, or its analogues, isoforms or derivatives, may be administered in any suitable myocardial event damage-inhibiting or -reducing amount. For example, Tβ4 may be administered in dosages within the range of about 0.1-50 micrograms of Tβ4, more preferably in amounts within the range of about 1-25 micrograms.

A composition in accordance with the present invention can be administered daily, every other day, etc., with a single administration or multiple administrations per day of administration, such as applications 2, 3, 4 or more times per day of administration.

Tβ4 isoforms have been identified and have about 70%, or about 75%, or about 80% or more homology to the known amino acid sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET [SEQ ID NO:1], that appears to be involved in mediating actin sequestration or binding. Although not wishing to be bound to any particular theory, the activity of Tβ4 isoforms may be due, in part, to the ability to regulate the polymerization of actin. β-thymosins appear to depolymerize F-actin by sequestering free G-actin. Tβ4's ability to modulate actin polymerization may therefore be due to all, or in part, its ability to bind to or sequester actin via the LKKTET [SEQ ID NO:1] sequence. Thus, as with Tβ4, other proteins which bind or sequester actin, or modulate actin polymerization, including Tβ4 isoforms having the amino acid sequence LKKTET [SEQ ID NO:1], are likely to be effective, alone or in a combination with Tβ4, as set forth herein.

Thus, it is specifically contemplated that known Tβ4 isoforms, such as Tβ4$^{ala}$, Tβ9, Tβ10, Tβ11, Tβ12, Tβ13, Tβ14 and Tβ15, as well as Tβ4 isoforms not yet identified, will be useful in the methods of the invention. As such Tβ4 isoforms are useful in the methods of the invention, including the methods practiced in a subject. The invention therefore further provides pharmaceutical compositions comprising Tβ4, as well as Tβ4 isoforms Tβ4$^{ala}$, Tβ9, Tβ10, Tβ11, Tβ12, Tβ13, Tβ14 and Tβ15, and a pharmaceutically acceptable carrier.

In addition, other proteins having actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET [SEQ ID NO:1], for example, can similarly be employed in the methods of the invention. Such proteins include gelsolin, vitamin D binding protein (DBP), profilin, cofilin, adsevertin, propomyosin, fincilin, depactin, Dnase1, vilin, fragmin, severin, capping protein, β-actinin and acumentin, for example. As such methods include those practiced in a subject, the invention further provides pharmaceutical compositions comprising gelsolin, vitamin D binding protein (DBP), profilin, cofilin, depactin, Dnase1, vilin, fragmin, severin, capping protein, β-actinin and acumentin as set forth herein. Thus, the invention includes the use of an angiogenesis-inducing, anti-inflammatory polypeptide comprising the amino acid sequence LKKTET [SEQ ID NO:1] (which may be within its primary amino acid sequence) and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Tβ4 has been localized to a number of tissue and cell types and thus, agents which stimulate the production of Tβ4 can be added to or comprise a composition to effect Tβ4 production from a tissue and/or a cell. Such agents include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α1 (Tα1) and vascular endothelial growth factor (VEGF). More preferably, the agent is transforming growth factor beta (TGF-β) or other members of the TGF-β superfamily. Tβ4 compositions of the invention may reduce the affects of myocardial events by effectuating growth of the connective tissue through extracellular matrix deposition, cellular migration and vascularization.

In accordance with one embodiment, subjects are treated with an agent that stimulates production in the subject of an angiogenesis-inducing, anti-inflammatory peptide as defined above.

Additionally, agents that assist or stimulate healing of damage caused by a myocardial event may be added to a composition along with Tβ4 or a Tβ4 isoform. Such agents include angiogenic agents, growth factors, agents that direct differentiation of cells. For example, and not by way of limitation, Tβ4 or a Tβ4 isoform alone or in combination can be added in combination with any one or more of the following agents: VEGF, KGF, FGF, PDGF, TGFβ, IGF-1, IGF-2, IL-1, prothymosin α and thymosin α1 in an effective amount.

The invention also includes a pharmaceutical composition comprising a therapeutically effective amount of Tβ4 or a Tβ4 isoform in a pharmaceutically acceptable carrier. Such carriers include those listed above with reference to parenteral administration.

The actual dosage, formulation or composition that heals or prevents inflammation, damage and degeneration associated with myocardial events may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

Suitable formulations include Tβ4 or a Tβ4 isoform at a concentration within the range of about 0.001-10% by weight, more preferably within the range of about 0.01-0.1% by weight, mostoreferably about 0.05% by weight.

The therapeutic approaches described herein involve various routes of administration or delivery of reagents or compositions comprising the Tβ4 or other compounds of the invention, including any conventional administration techniques to a subject. The methods and compositions using or containing Tβ4 or other compounds of the invention may be formulated into pharmaceutical compositions by admixture with pharmaceutically acceptable non-toxic excipients or carriers.

The invention includes use of antibodies which interact with Tβ4 peptide or functional fragments thereof. Antibodies which consists essentially of pooled monoclonal antibodies with different epitopic specificities, as well as distinct monoclonal antibody preparations are provided. Monoclonal antibodies are made from antigen containing fragments of the protein by methods well known to those skilled in the art as disclosed in PCT/US99/17282, supra. The term antibody as used in this invention is meant to include monoclonal and polyclonal antibodies.

In yet another embodiment, the invention provides a method of treating a subject by administering an effective amount of an agent which modulates Tβ4 gene expression. The term "modulate" refers to inhibition or suppression of Tβ4 expression when Tβ4 is over expressed, and induction of expression when Tβ4 is under expressed. The term "effective amount" means that amount of Tβ4 agent which is effective in modulating Tβ4 gene expression resulting in effective treatment. An agent which modulates Tβ4 or Tβ4 isoform gene expression may be a polynucleotide for example. The polynucleotide may be an antisense, a triplex agent, or a ribozyme. For example, an antisense directed to the structural gene region or to the promoter region of Tβ4 may be utilized.

In another embodiment, the invention provides a method for utilizing compounds that modulate Tβ4 activity. Compounds that affect Tβ4 activity (e.g., antagonists and agonists) include peptides, peptidomimetics, polypeptides, chemical compounds, minerals such as zincs, and biological agents.

While not be bound to any particular theory, the present invention may promote healing or prevention of inflammation or damage associated with myocardial events by inducing terminal deoxynucleotidyl transferase (a non-template directed DNA polymerase), to decrease the levels of one or more inflammatory cytokines, or chemokines, and to act as a chemotactic factor for endothelial cells, and thereby promoting healing or preventing degenerative changes in cardiac vessels and tissue brought about by myocardial event or other degenerative or environmental factors.

The invention is further illustrated by the following example, which is not to be construed as limiting.

EXAMPLE

Synthetic Tβ4 and an antibody to Tβ4 was provided by RegeneRx Biopharmaceuticals, Inc. (3 Bethesda Metro Center, Suite 700, Bethesda, Md. 20814) and were tested in a collagen gel assay to determine their effects on the Transformation of cardiac endothelial cells to mesenchymal cells. It is Well established that development of heart valves and other cardiac tissue are formed by epithelial-mesenchymal transformation and that defects in this process can cause serious cardiovascular malformation and injury during development and throughout life. At physiological concentrations Tβ4 markedly enhances the transformation of endocardial cells to mesenchymal cells in the collagen gel assay. Furthermore, an antibody to Tβ4 inhibited and blocked this transformation. Transformation of atrioventricular endocardium into invasive mesenchyme is critical in the formation and maintenance of normal cardiac tissue and in the formation of heart valves.

The invention claimed is:

1. A method of enhancing myocardial tissue cell differentiation in a subject in need thereof, wherein cardiac endothelial cells are transformed to mesenchymal cells, comprising administering to said subject a composition comprising an effective amount of thymosin beta 4 (Tβ4) and a pharmaceutically acceptable carrier, wherein said Tβ4 is administered in a dosage of about 0.1 to 50 micrograms and at a concentration of 0.001-10% by weight.

2. The method of claim 1 wherein said subject has damage to said cardiac tissue or vessels.

3. The method of claim 2 wherein said damage is to myocardium tissue.

4. The method of claim 2 wherein said damage is due to myocardial infarction or vessel occlusion.

5. The method of claim 2 wherein said subject has had a myocardial infarction.

6. The method of claim 1 wherein said subject is a mammal.

7. The method of claim 6 wherein said mammal is a human.

8. The method of claim 1 wherein said composition is administered directly to said cardiac tissue.

9. The method of claim 1 wherein said composition is administered systemically to said subject.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial
<220> FEATURE:
<223> OTHER INFORMATION: Homologous to Thymosin Beta 4

<400> SEQUENCE: 1

Leu Lys Lys Thr Glu Thr
1               5

<210> SEQ ID NO 2
<211> LENGTH: 7
<212> TYPE: PRT
<213> ORGANISM: Artificial
<220> FEATURE:
<223> OTHER INFORMATION: Homologous to Thymosin Beta 4

<400> SEQUENCE: 2

Lys Leu Lys Lys Thr Glu Thr
1               5

<210> SEQ ID NO 3
<211> LENGTH: 7
<212> TYPE: PRT
<213> ORGANISM: Artificial
<220> FEATURE:
<223> OTHER INFORMATION: Homologous to Thymosin Beta 4

<400> SEQUENCE: 3

Leu Lys Lys Thr Glu Thr Gln
1               5
```